United States Patent
Knappe et al.

(10) Patent No.: US 9,370,473 B2
(45) Date of Patent: Jun. 21, 2016

(54) POWDERY HAIR COSMETICS

(71) Applicant: Henkel AG & Co. KGaA, Dusseldorf (DE)

(72) Inventors: Thorsten Knappe, Schenefeld (DE); Anna Henschel, Winsen (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 142 days.

(21) Appl. No.: 14/364,955

(22) PCT Filed: Nov. 9, 2012

(86) PCT No.: PCT/EP2012/072236
§ 371 (c)(1),
(2) Date: Jun. 12, 2014

(87) PCT Pub. No.: WO2013/087311
PCT Pub. Date: Jun. 20, 2013

(65) Prior Publication Data
US 2014/0302106 A1    Oct. 9, 2014

(30) Foreign Application Priority Data
Dec. 16, 2011    (DE) .......................... 10 2011 088 840

(51) Int. Cl.
| | |
|---|---|
| *A61K 8/02* | (2006.01) |
| *A61Q 5/04* | (2006.01) |
| *A61K 9/14* | (2006.01) |
| *A61K 9/50* | (2006.01) |
| *A61K 8/34* | (2006.01) |
| *A61K 8/25* | (2006.01) |
| *A61Q 5/06* | (2006.01) |

(52) U.S. Cl.
CPC ................. *A61K 8/345* (2013.01); *A61K 8/022* (2013.01); *A61K 8/25* (2013.01); *A61Q 5/06* (2013.01); *A61K 2800/61* (2013.01); *A61K 2800/652* (2013.01)

(58) Field of Classification Search
None
See application file for complete search history.

(56) References Cited

U.S. PATENT DOCUMENTS

| | | | | |
|---|---|---|---|---|
| 2006/0246027 | A1* | 11/2006 | Tanner | A61K 8/0212 424/70.12 |
| 2012/0021028 | A1* | 1/2012 | Knappe | A61K 8/02 424/401 |
| 2015/0132244 | A1* | 5/2015 | Knappe | A61K 8/891 424/70.12 |

FOREIGN PATENT DOCUMENTS

| | | |
|---|---|---|
| DE | 102008057261 A1 | 5/2010 |
| WO | 0137800 A1 | 5/2001 |
| WO | 03037287 A1 | 5/2003 |
| WO | 2006056377 A1 | 6/2006 |
| WO | 2007051511 A1 | 5/2007 |
| WO | 2009120526 A1 | 10/2009 |
| WO | 2010054980 A1 | 5/2010 |
| WO | 2010115700 A2 | 10/2010 |
| WO | 2012168073 A1 | 12/2012 |

OTHER PUBLICATIONS

International Search Report completed Sep. 16, 2013 in PCT/EP2012/072236.

* cited by examiner

*Primary Examiner* — Jeffrey T Palenik
(74) *Attorney, Agent, or Firm* — P. Scott Smith

(57) ABSTRACT

Powdery compositions comprising core-shell particles are provided. The shell contains particles of at least one hydrophobized metal oxide powder and the liquid core contains, based on the weight of the core, about 20.0% by weight to 100.0% by weight, in particular about 50.0% by weight to 100.00% by weight, of at least one polyol of formula (I), wherein n represents an integer from 1 to 4. The powdery compositions are suitable for temporarily shaping keratin-containing fibers. For example, the use of said compositions on human hair resulted in an elastic hairstyle having volume. Hair so treated was given natural gloss.

15 Claims, No Drawings

POWDERY HAIR COSMETICS

CROSS REFERENCE TO RELATED APPLICATIONS

The present disclosure is a U.S. National Stage entry under 35 U.S.C. §371 based on International Application No. PCT/EP2012/072236, filed Nov. 9, 2012 which was published under PCT Article 21(2) and which claims priority to German Patent Application No. DE 10 2011 088 840.3 filed on Dec. 16, 2011, which is incorporated herein by reference in its entirety.

TECHNICAL FIELD

The technical field relates to temporary reshaping of keratin-containing fibers, in particular to temporary hair reshaping.

BACKGROUND

Styling agents for the deformation of keratinic fibers have been known for some time, and are employed in a variety of configurations to build up, refresh, and retain hairstyles that, for many hair types, can be obtained only using setting active agents. An important role is played here both by hair treatment agents that serve for permanent shaping of the hair, and by those that serve for temporary shaping. Temporary shaping results that are intended to produce good hold without negatively affecting the healthy appearance of the hair, for example its shine, can be obtained, for example, by means of hair sprays, hair waxes, hair gels, blow-dry waves, etc.

Corresponding agents for temporary shaping usually contain synthetic polymers as a shaping component. Preparations that contain a polymer can be applied onto the hair by means of propellant gases or using a pump mechanism. Hair gels and hair waxes, on the other hand, are as a rule not applied directly onto the hair but instead are distributed in the hair using a comb or the hands.

Known forms of temporary styling agents often cannot be metered with satisfactory accuracy. Hair gels, hair creams, and hair waxes, for example, are difficult to distribute once they have been applied onto the hair. As soon as the comb or the hands onto which the styling agent has been applied come into contact with the first hair areas, comparatively large quantities of styling agent are delivered onto the hair. Relatively little styling agent, on the other hand, is incorporated into hair areas that are reached only later with the comb or hands. The consequence of this is that the user either must from the outset apply a large quantity of styling agent so that even those hair areas reached last receive sufficient styling agent, or is forced to apply the styling agent in multiple steps, different hair areas being treated in each case. Hair sprays can be distributed more uniformly onto the hair. But because the user has no ability to visually perceive the total quantity of styling agent applied, the risk exists that more styling agent than would actually be necessary is applied onto the hair.

Powdered cosmetics are known and have already been used for some time, for example, in the skin treatment sector. Typical examples are make-up powder or eye shadow. The use of a powdered carrier material is necessary in order to achieve the powdered consistency. A metal oxide, for example silicon dioxide, can be used as a suitable carrier material. Hydrophobized metal oxide or silicon dioxide is of particular interest.

This can be obtained, for example, from pyrogenic silicon dioxide, which is commercially obtainable in various specifications. Untreated pyrogenic silicon dioxide carries silanol groups and siloxane groups on the surface. As a result, it has a high affinity for water, i.e. it is hydrophilic. By reaction with suitable organic silicon compounds, alkylsilyl groups can be chemically bound on the surface of the pyrogenic silicon dioxide. This results in modified silicon dioxide powders that can no longer be wetted by water, i.e. that have hydrophobic properties.

The use of hydrophobized silicon dioxide in cosmetics in order to produce so-called "dry water" for the skin is known to one skilled in the art. Here the hydrophobic properties of the modified silicon dioxide are exploited; the result of these properties is that when intensively mixed with water, the silicon dioxide is not simply dispersed in it. The water droplets are instead encased by the hydrophobic solid particles and prevented from coalescing again. Powdered solids having a water content of as much as 95% or more can thereby be obtained. Under mechanical stress, for example when rubbed onto the skin, the enclosed water is released again. This "dry water" is used as the basis for manufacturing shelf-stable solid hydrogen peroxide, and spreadable preparations having a very low oil content.

This concept is also the basis for the manufacture, described in EP 1 235 554 B1, of cosmetic or pharmaceutical liquefiable powder compositions. The powder compositions comprise hydrophobically coated silicon dioxide particles in which water and a water-soluble polymer are enclosed; the compositions contain less than 1% oil. The result of adding the water-soluble polymer is said to be that the powder feels pleasant and not grainy when used on the skin, without needing to add an oil component to the product for that purpose. The polymer is, for that purpose, added to the water phase in a quantity from 0.01 to 5 wt %, a concentration of only 0.1 to 1 wt % being preferred. The liquefiable powder compositions are employed chiefly for manufacturing decorative cosmetics. Utilization in deodorants or sun protection agents, or use on the hair as the basis of hair treatment agents that contain luster agents or care-providing components, is additionally described. Utilization in the sector of styling agents is not recited.

WO 03/037287 A1 discloses the use of a granulate based on pyrogenic silicon dioxide in cosmetic compositions. The special granulates can be silanized, i.e. hydrophobized, and are suitable for manufacturing cosmetic compositions of any consistency, for example liquids, foams, sprays, or powders. A plurality of conceivable cosmetics, among them hair-styling agents, are recited as possible cosmetic compositions. Only the usual application forms—lotion, hair spray, hair lacquer, hair gel, and hair wax—are recited, however. There is no indication that powdered styling agents might be manufactured on the basis of the silicon dioxide described.

The document WO 2007/051511 A1 discloses the use of a powdered composition containing 50 to 95 wt % of an aqueous solvent, hydrophobized silicon dioxide powder, and a film-forming and/or setting polymer at least present in the aqueous solvent, for the temporary deformation of keratinic fibers.

The document DE 102008057261 A1 relates to powdered compositions for the temporary reshaping of hair for a very strong hold on the retained hairstyle. Said powders comprise core-shell particles whose shell contains particles of at least one hydrophobized metal oxide powder and whose core comprises a liquid aqueous phase, characterized in that the powdered composition contains at least one film-forming and/or setting polymer in the form of particles.

The powdered hair cosmetics of the existing art by now provide a hold acceptable for hair reshaping. The result achieved with said agents, however, is capable of improvement in terms of the parameters of natural shine and the elasticity of the hold. In addition, most usual styling raw materials such as waxes, oils, or polymers are not readily suitable for manufacturing stable powdered compositions. Either they prevent successful formation of the core-shell particles, or the shelf stability of the core-shell particles that are formed is decreased.

At least one object herein was therefore to make available a powdered hair treatment agent for temporary shaping that
 can be metered accurately and simply,
 is shelf-stable,
 does not cause the hair to stick together,
 imparts a fuller and natural feel to the hair,
 imparts natural shine to the hair.
The durability of the styling result is intended not to be negatively affected.

SUMMARY

It has been found that the teaching of the existing art can be improved by a subsequently described powdered composition that contains in the liquid core a special polyol in a special quantity.

DETAILED DESCRIPTION

A first exemplary embodiment is powdered compositions for the temporary reshaping of keratin-containing fibers, in particular human hair, comprising core-shell particles whose shell contains particles of at least one hydrophobized metal oxide powder, and whose liquid core contains, based on the weight of the core, about 20.0 wt % to 100.0 wt %, in particular about 50.0 wt % to 100.0 wt %, of at least one polyol of formula (I)

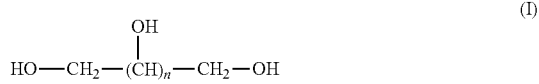

in which n denotes an integer from 1 to 4.

"Keratin-containing fibers" are to be understood in this context as furs, wool, feathers, and in particular human hair.

The core-shell particles of the powdered composition contemplated herein comprise a liquid core. Surrounding this liquid core is a shell that is based on separable individual particles of at least one hydrophobized metal oxide powder.

"Particles" are, for purposes herein, particles (cf. DIN 66160: 1992-09) of solids, which are present as grains.

Compositions whose particles are freely pourable under their own weight (cf. DIN EN ISO 6186: 1998-08) are "powdered" for purposes herein.

The powdered compositions contemplated herein are notable for the fact that as a result of a mechanical load on the core-shell particles, in particular as a result of friction and/or pressure, the liquid core becomes released from the core-shell particle and a liquid thereby forms from the powdered composition. This is thus a powdered powder-to-liquid composition. The powdered compositions contemplated herein can be metered very easily. They can furthermore be distributed very uniformly in hair, since the liquid core is released only under mechanical stress at the site of action, and controlled wetting of the hair fibers is enabled. The powder can thus firstly be carefully distributed in the hair and only then more strongly mechanically loaded, for example by deliberately massaging the powder into the hair. The styling effect is thus produced only directly on the desired hair area.

The powdered compositions that are used contain hydrophobized metal oxide. The nature of the hydrophobized metal oxide is in principle not limited, provided there is assurance that a corresponding core-shell particle is produced upon intensive mixing with the liquid aqueous phase. Those metal oxides which have been modified, at least on the surface of the particles, in such a way that the modified particles are wetted less by water than the unmodified particle, are to be understood as "hydrophobized" for purposes herein. Silanized hydrophobized metal oxides are particularly preferred. At least one representative of the group that is constituted from silanes, halosilanes, alkoxysilanes, and silazanes is preferably suitable according to the embodiments herein as a reagent for silanizing the metal oxide.

Preferably suitable hydrophobized metal oxides of the hydrophobized metal oxide powder are selected for use herein from at least one representative of the group that is constituted from hydrophobized silicates, hydrophobized aluminum silicates, hydrophobized titanium dioxide, and hydrophobized silicon dioxide.

Particularly preferred aluminum silicates (also called "aluminosilicates") are selected from phyllosilicates, tectosilicates, or mixtures thereof.

Preferably suitable phyllosilicates are selected from kaolins (in this case in particular from kaolinite, dickite, hallosite, and nacrite), serpentine, talc, pyrophyllite, montmorillonite, quartz, bentonite, mica (in this case in particular from illite, muscovite, paragonite, phlogopite, biotite, lepidolite, margarite, smectite (in this case in particular from montmorillonite, saponite, nontronite, hectorite)).

Preferably suitable tectosilicates are selected from feldspar minerals (in particular albite, orthoclase, anorthite, leucite, sodalite, hauyne, labradorite, lazurite, nosean, nepheline), zeolites.

The powdered compositions that are used contain the hydrophobized metal oxide powder preferably in a quantity from about 0.5 to about 30 wt %, based on the weight of the total powdered composition.

It has furthermore proven to be preferred if the hydrophobized metal oxides have a particle diameter of less than about 5 μm, preferably less than about 1 μm, particularly preferably between about 20 and about 100 nm.

Particularly preferably, the powdered composition contemplated herein contains as a hydrophobized metal oxide powder at least one hydrophobized silicon dioxide, in particular at least one silanized hydrophobized silicon dioxide.

At least one representative of the group that is constituted from silanes, halosilanes, alkoxysilanes, and silazanes is preferably suitable as a reagent for silanizing the silicon dioxide.

Preferred representatives of the group of silanes are hexa-($C_1$ to $C_m$) alkyldisilanes, in particular hexamethyldisilane.

If a halosilane is utilized as a silylating agent, the preferred halosilane selected is at least one compound from the group that is constituted from the compounds

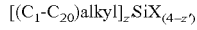

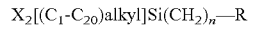

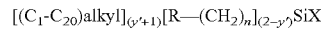

in which
X signifies a chlorine, bromine, or iodine atom,
z' is a number 1, 2, or 3,
y' is a number 0, 1, or 2,
n is an integer from 1 to 20, and
R denotes a residue from
($C_1$ to $C_{10}$) alkyl, aryl, ($C_1$ to $C_6$) perfluoroalkyl, —$NH_2$, —$N_3$, —SCN, —CH=$CH_2$,

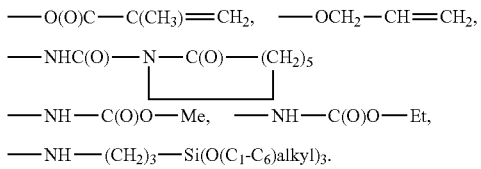

If an alkoxysilane is utilized as a silylating agent, the preferred alkoxysilane selected is at least one compound from the group that is constituted from the compounds

[($C_1$-$C_{20}$)alkylO]$_z$Si($C_1$-$C_{20}$)alkyl$_{(4-z)}$

[($C_1$-$C_{20}$)alkylO]$_z$Si[($CH_2$)$_n$—R]$_{(4-z)}$

[($C_1$-$C_{20}$)alkylO]$_2$[($C_1$-$C_{20}$)alkyl]Si($CH_2$)$_n$—R

[($C_1$-$C_{20}$)alkylO][($C_1$-$C_{20}$)alkyl]$_2$Si($CH_2$)$_n$—R

[($C_1$-$C_{20}$)alkylO][($C_1$-$C_{20}$)alkyl]Si($CH_2$)$_n$—$R_2$ ($C_1$-$C_{20}$ alkyl)$_3$SiO—C($CH_3$)=N—Si($C_1$-$C_{20}$)alkyl$_3$ in which
n is an integer from 1 to 20 and
z signifies a number 1, 2, or 3
R denotes a residue from
($C_1$ to $C_{20}$) alkyl, aryl, ($C_1$ to $C_6$) perfluoroalkyl, —$NH_2$, —$N_3$, —SCN, —CH=$CH_2$,

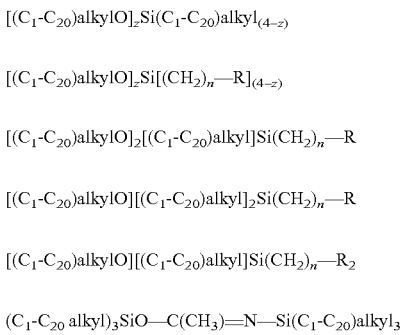

At least one compound from the class of disilazanes, in particular at least one compound from disilazanes of the formula R'$_2$R"Si—NH—SiR'$_2$R"

in which
R' signifies a ($C_1$ to $C_{20}$) alkyl group, and
R" signifies a ($C_1$ to $C_{20}$) alkyl group or a vinyl group, is preferably selected as a preferred silazane. A particularly preferred silazane is hexamethyldisilazane.

All the aforementioned alkyl groups, whether ($C_1$ to $C_6$) alkyl, ($C_1$ to $C_{10}$) alkyl, or ($C_1$ to $C_{20}$) alkyl, can be both cyclic and linear or branched. Examples of alkyl groups usable herein are methyl, ethyl, n-propyl, isopropyl, n-butyl, cyclopentyl, cyclohexyl, n-decyl, lauryl, myristyl, cetyl, stearyl, isostearyl, and behenyl.

An example of an aryl group useful herein is the phenyl group.

Examples of a ($C_1$ to $C_6$) perfluoroalkyl group are trifluoromethyl, perfluoroethyl, perfluoropropyl, and perfluorohexyl.

Hydrophobized silicon dioxides that are obtained by silanization of pyrogenic silicon dioxide are preferably employed.

Silanized hydrophobized silicon dioxides are particularly preferably selected from at least one compound of the group that is constituted from trimethyl silylate-coated silicon dioxide, dimethyl silylate-coated silicon dioxide, silicon dioxide, octyl silylate-coated silicon dioxide.

It is preferred in turn to select the hydrophobized metal oxide powder from silica silylates. These are hydrophobized silicon dioxides that conform to the INCI name Silica Silylate.

Those hydrophobized silicon dioxides which have a specific surface area according to BET between about 10 and about 400 m$^2$/g, preferably between about 80 and about 300 m$^2$/g, are preferred. Those hydrophobized silicon dioxides which are silanized, in particular Silica Silylate, are in turn preferably suitable.

A plurality of suitable hydrophobized silicon dioxides are commercially obtainable. Examples that can be recited are Aerosil® R104 V, Aerosil® R106, Aerosil® R202, Aerosil® R805, Aerosil® R812, Aerosil® R812S, Aerosil® R972, and Aerosil® R8200, all Degussa, and HDK® H2000, HDK® H2050, and HDK® H3004, all Wacker.

It is particularly preferred to use the hydrophobized silicon dioxides that are obtainable under the names Aerosil® 8202, Aerosil® R812S, or Aerosil® R972. The silicon dioxide having the INCI name Silica Silylate, which is marketed by the Degussa company under the name Aerosil® R812S, is very particularly preferably used.

The powdered compositions that are used contain the hydrophobized silicon oxide powder preferably in a quantity from about 0.5 to about 30 wt %, based on the weight of the total powdered composition.

It is particularly preferred in turn to select the hydrophobized silicon dioxide powder from Silica Silylate, and to use it in a quantity from about 0.5 to about 30 wt %, based on the weight of the total powdered composition in the composition.

The optimum quantity here depends chiefly on the hydrophobicity of the silicon dioxide powder used. The more hydrophobic the silicon dioxide powder, the less thereof is needed in order to obtain a stable powdered product.

The powdered composition contemplated herein preferably contains as a hydrophobized metal oxide at least one hydrophobized phyllosilicate, in particular at least one hydrophobized mica and/or at least one hydrophobized talc. At least one silanized hydrophobized phyllosilicate or at least one silanized hydrophobized mica, and/or at least one hydrophobized talc, is in turn preferably suitable.

At least one representative of the group that is constituted from silanes, halosilanes, alkoxysilanes, and silazanes is preferably suitable as a reagent for silanizing the phyllosilicate or mica. For the particularly preferred reagents, reference is made, mutatis mutandis, to the statements regarding the silanization of silicon dioxide (see above).

Silanized hydrophobized micas are selected particularly preferably from at least one compound of the group that is constituted from trimethyl silylate-coated mica, dimethyl silylate-coated mica, octyl silylate-coated mica.

Silanized hydrophobized talc is selected particularly preferably from at least one compound of the group that is constituted from trimethyl silylate-coated talc, dimethyl silylate-coated talc, octyl silylate-coated talc.

Hydrophobized mica silanized with triethoxycaprylsilane, hydrophobized talc silanized with triethoxycaprylsilane, for example from the LCW company, are to be recited, for example, as a hydrophobically modified phyllosilicate usable herein.

The powdered compositions that are used contain hydrophobized mica and/or hydrophobized talc preferably in a quantity from about 0.5 to about 30 wt %, based on the weight of the total powdered composition.

The powdered compositions contemplated herein furthermore obligatorily contain at least one polyol of the above formula (I) in the quantity indicated. It has proven to be preferred if the polyol of formula (I) is selected from at least one compound of the group that is constituted from glycerol, threitol, erythritol, sorbitol, arabitol, altritol, ribitol, xylitol, galactitol, mannitol, iditol. If said polyols are present as stereoisomers, the D form, the L form, and the D,L form are suitable; the D form is preferred in each case due to its availability. A very particularly preferred polyol of formula (I) is glycerol.

The liquid core can additionally contain, besides the aforesaid polyol of formula (I), at least one further solvent. This is preferred in particular when the polyols of formula (I) that are used are exclusively those which are present in the form of a solid at 20° C. and a pressure of 1 atm. The additional solvents are contained in the powdered composition contemplated herein preferably in a quantity from 0 to about 40 wt %, particularly preferably from 0 to about 20 wt %, very particularly preferably from 0 to about 10 wt %, based in each case on the weight of the liquid core.

The additional solvent is of course different from the compounds of the above formula (I). Water, or a mixture of water and a maximum of about 60 wt % $C_1$ to $C_4$ alcohol, based on the solvent mixture, is preferably employed as an additional solvent. Particularly preferred additional solvents are water or a mixture of water and a maximum of about 30 wt % $C_1$ to $C_4$ alcohol, based on the solvent mixture. Water, in particular in the preferred quantities indicated above for the additional solvent, is very particularly preferably used as an additional solvent.

The following embodiments (A) to (P) are particularly preferably suitable.

(A): Powdered compositions comprising core-shell particles whose shell contains particles of at least one hydrophobized metal oxide powder, and whose liquid core contains, based on the weight of the core, about 20.0 wt % to 100.0 wt %, in particular about 50.0 wt % to 100.0 wt % of at least one polyol of formula (I)

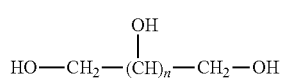

in which n denotes an integer from 1 to 4.

(B): Powdered compositions comprising core-shell particles
whose shell contains particles of at least one hydrophobized metal oxide powder made of at least one representative of the group that is constituted from hydrophobized silicates, hydrophobized aluminum silicates, hydrophobized titanium dioxide, and hydrophobized silicon dioxide, and
whose liquid core contains, based on the weight of the core, about 20.0 wt % to 100.0 wt %, in particular about 50.0 wt % to 100.0 wt % of at least one polyol of formula (I)

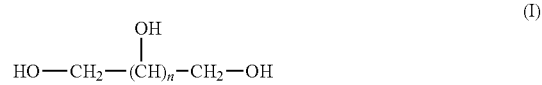

in which n denotes an integer from 1 to 4.

(C): Powdered compositions comprising core-shell particles whose shell contains particles of at least one hydrophobized metal oxide powder, and whose liquid core contains, based on the weight of the core, about 20.0 wt % to 100.0 wt %, in particular about 50.0 wt % to 100.0 wt % glycerol.

(D): Powdered compositions comprising core-shell particles
whose shell contains particles of at least one hydrophobized metal oxide powder made of at least one representative of the group that is constituted from hydrophobized silicates, hydrophobized aluminum silicates, hydrophobized titanium dioxide, and hydrophobized silicon dioxide, and
whose liquid core contains, based on the weight of the core, about 20.0 wt % to 100.0 wt %, in particular about 50.0 wt % to 100.0 wt % glycerol.

(E): Powdered compositions comprising core-shell particles whose shell contains particles of at least one hydrophobized metal oxide powder, and whose liquid core contains, based on the weight of the core,
(i) about 20.0 wt % to 100.0 wt %, in particular about 50.0 wt % to 100.0 wt % of at least one polyol of formula (I)

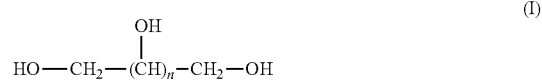

in which n denotes an integer from 1 to 4, and
(ii) 0 to 60 wt %, in particular 0 to 40 wt % water.

(F): Powdered compositions comprising core-shell particles
whose shell contains particles of at least one hydrophobized metal oxide powder made of at least one representative of the group that is constituted from hydrophobized silicates, hydrophobized aluminum silicates, hydrophobized titanium dioxide, and hydrophobized silicon dioxide, and
whose liquid core contains, based on the weight of the core,
(i) about 20.0 wt % to 100.0 wt %, in particular about 50.0 wt % to 100.0 wt % of at least one polyol of formula (I)

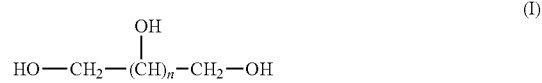

in which n denotes an integer from 1 to 4, and
(ii) 0 to about 60 wt %, in particular 0 to about 40 wt % water.

(G): Powdered compositions comprising core-shell particles whose shell contains particles of at least one hydrophobized metal oxide powder, and whose liquid core contains, based on the weight of the core,
(i) about 20.0 wt % to 100.0 wt %, in particular about 50.0 wt % to 100.0 wt % glycerol, and
(ii) 0 to about 60 wt %, in particular 0 to about 10 wt % water.

(H): Powdered compositions comprising core-shell particles
whose shell contains particles of at least one hydrophobized metal oxide powder made of at least one representative of the group that is constituted from hydrophobized silicates, hydrophobized aluminum silicates, hydrophobized titanium dioxide, and hydrophobized silicon dioxide, and
whose liquid core contains, based on the weight of the core,
(i) about 20.0 wt % to 100.0 wt %, in particular about 50.0 wt % to 100.0 wt % glycerol, and
(ii) 0 to about 60 wt %, in particular 0 to about 10 wt % water.

(I): Powdered compositions comprising core-shell particles whose shell contains, based on the weight of the powdered composition, about 0.5 to about 30.0 wt % particles of at least one hydrophobized metal oxide powder, and whose liquid core contains, based on the weight of the core, about 20.0 wt % to 100.0 wt %, in particular about 50.0 wt % to 100.0 wt % of at least one polyol of formula (I)

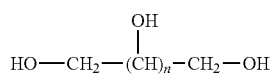
(I)

in which n denotes an integer from 1 to 4.

(J): Powdered compositions comprising core-shell particles
whose shell contains, based on the weight of the powdered composition, about 0.5 to about 30.0 wt % particles of at least one hydrophobized metal oxide powder made of at least one representative of the group that is constituted from hydrophobized silicates, hydrophobized aluminum silicates, hydrophobized titanium dioxide, and hydrophobized silicon dioxide, and
whose liquid core contains, based on the weight of the core, about 20.0 wt % to 100.0 wt %, in particular about 50.0 wt % to 100.0 wt % of at least one polyol of formula (I)

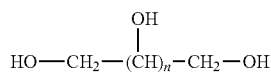
(I)

in which n denotes an integer from 1 to 4.

(K): Powdered compositions comprising core-shell particles whose shell contains, based on the weight of the powdered composition, about 0.5 to about 30.0 wt % particles of at least one hydrophobized metal oxide powder, and whose liquid core contains, based on the weight of the core, about 20.0 wt % to 100.0 wt %, in particular about 50.0 wt % to 100.0 wt % glycerol.

(L): Powdered compositions comprising core-shell particles
whose shell contains, based on the weight of the powdered composition, about 0.5 to about 30.0 wt % particles of at least one hydrophobized metal oxide powder made of at least one representative of the group that is constituted from hydrophobized silicates, hydrophobized aluminum silicates, hydrophobized titanium dioxide, and hydrophobized silicon dioxide, and
whose liquid core contains, based on the weight of the core, about 20.0 wt % to 100.0 wt %, in particular about 50.0 wt % to 100.0 wt % glycerol.

(M): Powdered compositions comprising core-shell particles whose shell contains, based on the weight of the powdered composition, about 0.5 to about 30.0 wt % particles of at least one hydrophobized metal oxide powder, and whose liquid core contains, based on the weight of the core,
(i) about 20.0 wt % to 100.0 wt %, in particular about 50.0 wt % to 100.0 wt % of at least one polyol of formula (I)

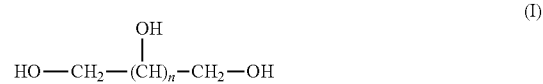
(I)

in which n denotes an integer from 1 to 4, and
(ii) 0 to about 60 wt %, in particular 0 to about 40 wt % water.

(N): Powdered compositions comprising core-shell particles
whose shell contains, based on the weight of the powdered composition, about 0.5 to about 30.0 wt % particles of at least one hydrophobized metal oxide powder made of at least one representative of the group that is constituted from hydrophobized silicates, hydrophobized aluminum silicates, hydrophobized titanium dioxide, and hydrophobized silicon dioxide, and
whose liquid core contains, based on the weight of the core,
(i) about 20.0 wt % to 100.0 wt %, in particular about 50.0 wt % to 100.0 wt % of at least one polyol of formula (I)

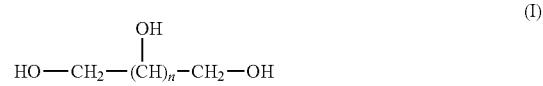
(I)

in which n denotes an integer from 1 to 4, and
(ii) 0 to about 60 wt %, in particular 0 to about 40 wt % water.

(O): Powdered compositions comprising core-shell particles whose shell contains, based on the weight of the powdered composition, about 0.5 to about 30.0 wt % particles of at least one hydrophobized metal oxide powder, and whose liquid core contains, based on the weight of the core,
(i) about 20.0 wt % to 100.0 wt %, in particular about 50.0 wt % to 100.0 wt % glycerol, and
(ii) 0 to about 60 wt %, in particular 0 to about 10 wt % water.

(P): Powdered compositions comprising core-shell particles
whose shell contains, based on the weight of the powdered composition, about 0.5 to about 30.0 wt % particles of at least one hydrophobized metal oxide powder made of at least one representative of the group that is constituted from hydrophobized silicates, hydrophobized aluminum silicates, hydrophobized titanium dioxide, and hydrophobized silicon dioxide, and
whose liquid core contains, based on the weight of the core,
(i) about 20.0 wt % to 100.0 wt %, in particular about 50.0 wt % to 100.0 wt % glycerol, and (ii) 0 to about 60 wt %, in particular 0 to about 10 wt % water.

The aforesaid preferred embodiments of the ingredients (see above) are in turn considered preferred, mutatis mutandis, for the embodiments (A) to (P). In particular, at least one hydrophobized silicon dioxide, in particular at least one silanized hydrophobized silicon dioxide, is employed in the context of the preferred embodiments (A) to (P) as a preferred hydrophobized metal oxide powder.

The liquid aqueous phase can in addition preferably contain those additives which do not significantly reduce the surface tension of the aqueous phase. It is therefore preferred if the powdered compositions contemplated herein contain in the liquid core no more than about 0.01 wt % surfactants, based on the weight of the powdered composition.

In order to improve feel, the powdered composition contemplated herein can additionally contain at least one mineral salt. Preferred mineral salts are selected from hygroscopic mineral salts such as, in particular, calcium chloride, magnesium chloride, magnesium sulfate, and sodium sulfate. The mineral salts are in turn contained, based on the weight of the powdered composition, preferably in a quantity from about 1.0 to about 30.0 wt %, in particular from about 4.0 to about 25 wt %.

In order to improve hair care, the powdered compositions can preferably contain at least one care-providing substance, which is preferably present in the liquid aqueous phase.

The powdered compositions contemplated herein can contain at least one UV filter as a care-providing substance. The UV filters suitable herein are not subject to any general restrictions in terms of their structure and their physical properties. Instead, all UV filters usable in the cosmetics sector, whose absorption maximum lies in the UVA (315 to 400 nm), UVB (280 to 315 nm), or UVC (<280 nm) regions, are suitable. UV filters having an absorption maximum in the UVB region, in particular in the region from approximately 280 to approximately 300 nm, are particularly preferred.

Those UV filters whose molar extinction coefficient at the absorption maximum is above 15,000, in particular above 20,000, are preferred.

It has furthermore been found that with structurally similar UV filters, the water-insoluble compound in many cases exhibits the greater effectiveness as compared with those water-soluble compounds which differ from it by having one or more additionally ionic groups. In the context herein, those UV filters of which no more than about 1 wt %, in particular no more than about 0.1 wt %, dissolves in water at 20° C., are understood to be "water-insoluble." These compounds should furthermore be soluble at a proportion of at least about 0.1, in particular at least about 1 wt %, in common cosmetic oil components at room temperature. The use of water-insoluble UV filters can therefore be preferred herein.

Two preferred UV filters having cationic groups are the compounds cinnamic acid amidopropyltrimethylammonium chloride (Incroquat® UV-283) and dodecyldimethylaminobenzamidopropyldimethylammonium tosylate (Escalol® HP 610), available as commercial products.

The powdered compositions contemplated herein of course also encompasses the use of a combination of several UV filters. In the context of this embodiment, the combination of at least one water-insoluble UV filter with at least one UV filter having a cationic group is preferred.

The UV filters are contained in the powdered compositions usually in quantities from about 0.01 to about 5 wt % based on the powdered composition. Quantities from about 0.1 to about 2.5 wt % are preferred.

The preparations preferably contain at least one vitamin, provitamin, vitamin precursor, and derivative thereof as an additional care-providing substance.

Those vitamins, provitamins, and vitamin precursors which are usually assigned to the groups A, B, C, E, F, and H are preferred.

Vitamin H. "Vitamin H" refers to the compound (3aS,4S, 6aR)-2-oxohexahydrothienol[3,4-d]-imidazole-4-valeric acid, for which the trivial name "biotin" has, however, now become established. Biotin is a vitamin very particularly preferred. The use of biotin in the preparations herein has made it possible, surprisingly, to improve restructuring of the fibers, achieve structural stabilization, and substantially reduce the irritation potential of the agents. Biotin is contained in the powdered compositions contemplated herein preferably in quantities from about 0.0001 to about 2.0 wt %, in particular in quantities from about 0.001 to about 0.2 wt %, based in each case on the powdered composition.

The powdered compositions preferably contain vitamins, provitamins, and vitamin precursors from groups A, B, C, E, and H. Vitamin C can be very particularly preferred.

Panthenol, pantolactone, pyridoxine, derivatives of pyridoxine, nicotinic acid amide, biotin, and mixtures thereof are care-providing substances particularly preferred.

The powdered compositions contemplated herein can contain at least one plant extract as a care-providing substance.

These extracts are usually produced by extraction of the entire plant. In individual cases, however, it can also be preferred to produce the extracts exclusively from blossoms and/or leaves of the plant.

The extracts from Moringa olefeira, green tea, oak bark, stinging nettle, witch hazel, hops, chamomile, burdock, horsetail, linden blossom, almond, aloe vera, coconut, mango, apricot, lemon, wheat, kiwi, melon, orange, grapefruit, sage, rosemary, birch, lady's smock, wild thyme, yarrow, restharrow, meristem, ginseng, and ginger root are particularly preferred. The extracts from Moringa olefeira, green tea, almond, aloe vera, coconut, mango, apricot, lemon, wheat, kiwi, and melon are very particularly suitable. Water, alcohol, and mixtures thereof can be used as extraction agents for producing the aforesaid plant extracts. Among the alcohols, lower alcohols such as ethanol and isopropanol, but in particular polyvalent alcohols such as ethylene glycol and propylene glycol, both as the only extraction agent and mixed with water, are preferred. Plant extracts based on water/propylene glycol at a ratio from 1:10 to 10:1 have proven particularly suitable. As used herein, the plant extracts can be used in both pure and diluted form. If they are used in diluted form, they usually contain approx. 2 to approx. 80 wt % active substance, and contain as a solvent the extraction agent or extraction agent mixture used to recover them.

It can further be preferred to use in the preparations contemplated herein mixtures of several, in particular two, different plant extracts.

The powdered compositions can contain as a care-providing substance at least one protein hydrolysate and/or one derivative thereof Protein hydrolysates are product mixtures obtained by the acid-, base-, or enzyme-catalyzed breakdown of proteins. The term "protein hydrolysates" is also understood herein to mean total hydrolysates and individual amino acids and derivatives thereof, as well as mixtures of different amino acids. Polymers constructed from amino acids and amino-acid derivatives are also understood herein under the term "protein hydrolysates". Included among the latter are, for example, polyalanine, polyasparagine, polyserine, etc. Further examples of compounds usable according to the present invention are L-alanyl-L-proline, polyglycine, glycyl-L-glutamine, or D/L-methionine-S-methylsulfonium chloride. β-Amino acids and derivatives thereof, such as β-alanine, anthranilic acid, or hippuric acid, can of course also be used herein. The molecular weight of the protein hydrolysates for use herein is between about 75 (the molecular weight of glycine) and about 200,000; the molecular weight is preferably about 75 to about 50,000, and very particularly preferably about 75 to about 20,000 dalton. Protein hydrolysates of both vegetable and animal origin, or of marine or synthetic origin, can be used.

Animal protein hydrolysates are, for example, protein hydrolysates of elastin, collagen, keratin, silk, and milk protein, which can also be present in the form of salts. Such products are marketed, for example, under the trademarks Dehylan® (Cognis), Promois® (Interorgana), Collapuron® (Cognis), Nutrilan® (Cognis), Gelita-Sol® (Deutsche Gelatine Fabriken Stoess & Co), Lexein® (Inolex), Sericin (Pentapharm), and Kerasol® (Croda). It is preferred to use protein hydrolysates of vegetable origin, for example soy, almond, pea, potato, and wheat protein hydrolysates. Such products are obtainable, for example, under the trademarks Gluadin® (Cognis), DiaMin® (Diamalt), Lexein® (Inolex), Hydrosoy® (Croda), Hydrolupin® (Croda), Hydrosesame® (Croda), Hydrotritium® (Croda), and Crotein® (Croda).

Although the use of protein hydrolysates as such is preferred, amino acid mixtures obtained in other ways can also optionally be used instead of them.

All isomeric forms, such as cis-trans isomers, diastereomers, and chiral isomers can be used.

It is also possible to employ a mixture of several protein hydrolysates.

In the context of a ninth preferred embodiment, the preparations herein contain ectoin or ectoin derivatives, allantoin, taurine, and bisabolol as a care-providing substance.

The term "amino acid" is understood as the stereoisomeric forms, e.g. D- and L-forms, of the following compounds: asparagine, arginine, aspartic acid, glutamine, glutamic acid, β-alanine, γ-aminobutyrate, $N_\epsilon$-acetyllysine, $N_\delta$-acetylornithine, $N_\gamma$-acetyldiaminobutyrate, $N_\alpha$-acetyldiaminobutyrate, histidine, isoleucine, leucine, methionine, phenylalanine, serine, threonine and tyrosine.

L-amino acids are preferred. Amino-acid residues are derived from the corresponding amino acids. The following amino-acid residues are preferred: Gly, Ala, Ser, Thr, Val, β-Ala, γ-aminobutyrate, Asp, Glu, Asn, Aln, $N_\epsilon$-acetyllysine, $N_\delta$-acetylornithine, $N_\gamma$-acetyldiaminobutyrate, $N_\alpha$-acetyldiaminobutyrate.

The amino acids have been abbreviated in accordance with generally usual notation. The di- or tripeptide radicals are acid amides in terms of their chemical nature, and decompose into two or three amino acids upon hydrolysis. The amino acids in the di- or tripeptide residue are joined to one another by amide bonds.

The powdered compositions contemplated herein contain these active agents preferably in quantities from about 0.001 to about 2, in particular from about 0.01 to about 0.5 wt %, based in each case on the powdered composition.

All the aforesaid preferred optional care-providing substances are preferably a constituent of the liquid core of the powdered compositions.

The powdered compositions contemplated herein preferably additionally contain at least one setting polymer. The setting polymers can be present in dispersed or dissolved form in the liquid core, and/or the setting polymers are, as a particulate solid, a constituent of the shell of the core-shell particles.

"Polymers" are understood herein as compounds that are constructed from a plurality of molecules in which one type or several types of atoms or atom groupings (so-called "constituent units," "basic modules," or "repeating units") are repeatedly serially arranged, and that possess a molecular weight of at least about 10,000 g/mol. Polymers are obtained by polyreaction, which latter can be accomplished artificially (i.e. synthetically) or naturally.

Setting polymers contribute to the hold, and/or to buildup of the hair volume and hair fullness, of the overall hairstyle. These polymers are at the same time also film-forming polymers and are therefore generally typical substances for shape-imparting hair treatment agents such as hair setting agents, hair foams, hair waxes, hair sprays. It is certainly possible for film formation to be localized, and for only a few fibers to be connected to one another.

"Film-forming polymers" are to be understood as those polymers which, upon drying, leave behind a continuous film on the skin, hair, or nails. Film-formers of this kind can be used in a very wide variety of cosmetic products, for example face masks, make-up, hair setting agents, hair sprays, hair gels, hair waxes, hair therapies, shampoos, or nail polishes. Those polymers which possess sufficient solubility in water, alcohol, or water/alcohol mixtures are particularly preferred. This allows the production of corresponding solutions that can be easily utilized or further processed.

"Film-forming polymers" are furthermore understood as those polymers which, when used in an about 0.01 to about 20 wt % aqueous, alcoholic, or aqueous alcoholic solution, are capable of depositing a transparent polymer film onto the hair.

The additional setting polymers are preferably contained in a quantity from about 0.1 wt % to about 10 wt %, in particular from about 1.0 wt % to about 8.0 wt %, very particularly preferably from about 2.0 to about 6.0 wt %, based in each case on the weight of the powdered composition.

In the context of a particularly preferred embodiment, the powdered compositions contain at least one nonionic setting polymer as an additional film-forming and/or setting polymer.

The additional nonionic setting polymers are contained in the powdered compositions contemplated herein preferably in a quantity from about 0.1 wt % to about 10 wt %, particularly preferably from about 1.0 wt % to about 8.0 wt %, very particularly preferably from about 2.0 to about 6.0 wt %, based in each case on the weight of the powdered composition.

The nonionic setting polymers are in turn preferably selected from at least one polymer of the group that is constituted from
   homopolymers and nonionic copolymers of N-vinylpyrrolidone,
   nonionic copolymers of isobutene,
   nonionic copolymers of maleic acid anhydride.

Suitable polyvinylpyrrolidones are, for example, commercial products such as Luviskol® K 90 or Luviskol® K 85 of the BASF SE company.

Suitable polyvinyl acetate is marketed, for example, by the Air Products company as an emulsion under the commercial name Vinac®.

Powdered compositions contemplated herein that contain as a nonionic setting polymer at least one polymer selected from the group that is constituted from
   copolymers of maleic acid anhydride and methyl vinyl ether, polyvinylpyrrolidone,
copolymers of N-vinylpyrrolidone and vinyl esters of carboxylic acids having 2 to 18 carbon atoms, in particular of N-vinylpyrrolidone and vinyl acetate,
or mixtures of said polymers, are very particularly preferred. Those powdered compositions that contain as a nonionic setting polymer at least one polymer selected from the group that is constituted from
polyvinylpyrrolidone,
copolymers of N-vinylpyrrolidone and vinyl esters of carboxylic acids having 2 to 18 carbon atoms, in particular of N-vinylpyrrolidone and vinyl acetate,
or mixtures of said polymers, are in turn preferred.

If copolymers of N-vinylpyrrolidone and vinyl esters of carboxylic acids having 2 to 18 carbon atoms, in particular of N-vinylpyrrolidone and vinyl acetate, are employed, it is in turn preferred if the molar ratio of the structural units of the polymer contained from the N-vinylpyrrolidone monomer to the structural units of the polymer contained from the vinyl acetate monomer is in the range from about 20 to 80 to about 80 to 20, in particular from about 30 to 70 to about 60 to 40.

Suitable copolymerizates of vinylpyrrolidone and vinyl acetate are obtainable, for example, from the BASF SE company under the trademarks Luviskol® VA 37, Luviskol® VA 55, Luviskol® VA 64, and Luviskol® VA 73.

The powdered compositions contemplated herein preferably contain at least one cationic setting polymer as an additional setting polymer. "Cationic" polymers are to be understood as polymers that comprise in the main chain and/or side chain a group that can be "temporarily" or "permanently" cationic. Those polymers which comprise a cationic group regardless of the pH of the agent are referred to as "permanently cationic." These are, as a rule, polymers that contain a quaternary nitrogen atom, for example in the form of an ammonium group. Preferred cationic groups are quaternary ammonium groups. Those polymers in particular in which the quaternary ammonium group is bonded via a C1-4 hydrocarbon group to a main polymer chain constructed from acrylic acid, methacrylic acid, or derivatives thereof, have proven particularly suitable.

A cationic setting polymer preferably suitable herein is at least one cationic setting polymer that contains at least one structural element of formula (M9) and additionally at least one structural element of formula (M10)

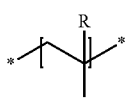

(M9)

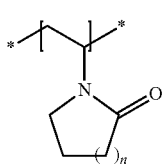

(M10)

in which

R denotes a hydrogen atom or a methyl group,

R', R'', and R''' mutually independently denote a ($C_1$ to $C_{30}$) alkyl group, X denotes an oxygen atom or an NH group, A denotes an ethane-1,2-diyl group or a propane-1,3-diyl group, n signifies 1 or 3.

All possible physiologically acceptable anions, for example chloride, bromide, hydrogen sulfate, methyl sulfate, ethyl sulfate, tetrafluoroborate, phosphate, hydrogen phosphate, dihydrogen phosphate, or p-toluenesulfonate, triflate, serve to compensate for the positive polymer charge.

Such compounds are, for example, as copolymers of dimethylaminoethyl methacrylate, quaternized with diethyl sulfate, with vinylpyrrolidone, having the INCI name Polyquaternium-11, under the designations Gafquat® 440, Gafquat® 734, Gafquat® 755 (each ISP company) and Luviquat PQ 11 PN (BASF SE), copolymers of N-vinylpyrrolidone, N-(3-dimethylaminopropyl) methacrylamide), and 3-(methacryloylamino) propyllauryldimethylammonium chloride (NCI name: Polyquaternium-55), which are marketed e.g. under the commercial name Styleze W-10 or Styleze W 20 (10 or 20 wt % active substance in ethanol-water mixture) by the ISP company, copolymers of N-vinylpyrrolidone, N-vinylcaprolactam, N-(3-dimethylaminopropyl) methacrylamide, and 3-(methacryloylamino)propyllauryldimethylammonium chloride (INCI name: Polyquaternium-69), which are marketed e.g. under the commercial name Aqua-Style® 300 (28 to 32 wt % active substance in ethanol-water mixture) by the ISP company.

Those cationic setting polymers which comprise at least one structural element of formula (M11)

(M11)

in which R'' denotes a ($C_1$ to $C_4$) alkyl group, in particular a methyl group, and additionally at least one further cationic and/or nonionic structural element, furthermore serve as cationic polymers that are particularly preferably usable herein.

All possible physiologically acceptable anions, for example chloride, bromide, hydrogen sulfate, methyl sulfate, ethyl sulfate, tetrafluoroborate, phosphate, hydrogen phosphate, dihydrogen phosphate, or p-toluenesulfonate, triflate, serve to compensate for the positive polymer charge.

It is in turn preferred according to embodiments if at least one copolymer (c1), which comprises besides at least one structural element of formula (M11) additionally a structural element of formula (M6)

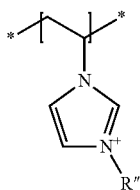
(M11)

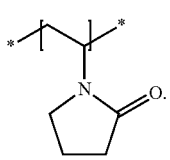
(M6)

in which R" denotes a ($C_1$ to $C_4$) alkyl group, in particular a methyl group, is contained as an additional cationic setting polymer.

All possible physiologically acceptable anions, for example chloride, bromide, hydrogen sulfate, methyl sulfate, ethyl sulfate, tetrafluoroborate, phosphate, hydrogen phosphate, dihydrogen phosphate, or p-toluenesulfonate, triflate, serve to compensate for the positive polymer charge of copolymers (c1).

Very particularly preferred cationic setting polymers as copolymers (c1) contain about 10 to about 30 mol %, preferably about 15 to about 25 mol %, and in particular about 20 mol % structural units in accordance with formula (M11) and about 70 to about 90 mol %, preferably about 75 to about 85 mol %, and in particular about 80 mol % structural units in accordance with formula (M6).

It is particularly preferred in this context if copolymers (c1) contain, besides polymer units that result from incorporation of the aforesaid structural units in accordance with formulas (M11) and (M6) into the copolymer, a maximum of about 5 wt %, preferably a maximum of about 1 wt % polymer units that are based on the incorporation of other monomers. Copolymers (c1) are preferably constructed exclusively from structural units of formula (M11), where R"=methyl, and (M6).

If a chloride ion is used to compensate for the positive charge of the polymer of formula (Poly1), these N-methylvinylimidazole/vinylpyrrolidone copolymers are then referred to according to INCI nomenclature as Polyquaternium-16 and are e.g. from BASF under the commercial names Luviquat® Style, Luviquat® FC 370, Luviquat® FC 550, Luviquat® FC 905, and Luviquat® HM 552.

If a methosulfate is used to compensate for the positive charge of the polymer of formula (Poly1), these N-methylvinylimidazole/vinylpyrrolidone copolymers are then referred to according to INCI nomenclature as Polyquaternium-44 and are obtainable e.g. from BASF under the commercial names Luviquat® UltraCare.

In addition to or instead of the copolymer or copolymers (c1), the powdered compositions contemplated herein can also contain copolymers (c2) that, proceeding from copolymer (c1), contain as additional structural units those of formula (M7)

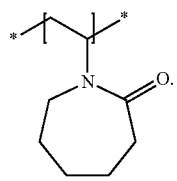
(M7)

Further particularly preferred powdered compositions are thus characterized in that they contain as a cationic setting polymer at least one copolymer (c2) that contains at least one structural unit in accordance with formula (M11-a) and at least one structural unit in accordance with formula (M6) and at least one structural unit in accordance with formula (M7).

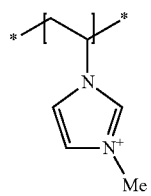
(M11-a)

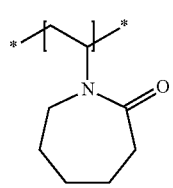
(M6)

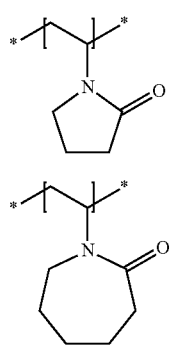
(M7)

Here as well, it is particularly preferred if copolymers (c2) contain, besides polymer units that result from the incorporation of the aforesaid structural units in accordance with formulas (M11-a), (M6), and (M7) into the copolymer, a maximum of about 5 wt %, preferably a maximum of about 1 wt % polymer units that are based on the incorporation of other monomers. Copolymers (c2) are preferably constructed exclusively from structural units of formulas (M11-a), (M6), and (M7).

All possible physiologically acceptable anions, for example chloride, bromide, hydrogen sulfate, methyl sulfate, ethyl sulfate, tetrafluoroborate, phosphate, hydrogen phosphate, dihydrogen phosphate, or p-toluenesulfonate, triflate, serve to compensate for the positive polymer charge of component (c2).

If a methosulfate is used to compensate for the positive charge of the polymer of formula (Poly2), these N-methylvinylimidazole/vinylpyrrolidone/vinylcaprolactam copolymers are referred to according to INCI nomenclature as Polyquaternium-46 and are obtainable e.g. from BASF under the commercial name Luviquat® Hold.

Very particularly preferred copolymers (c2) contain about 1 to about 20 mol %, preferably about 5 to about 15 mol %, and in particular about 10 mol % structural units in accordance with formula (M11-a) and about 30 to about 50 mol %, preferably about 35 to about 45 mol %, and in particular about 40 mol % structural units in accordance with formula (M6) and about 40 to about 60 mol %, preferably about 45 to about 55 mol %, and in particular about 60 mol % structural units in accordance with formula (M7).

In addition to or instead of the copolymer or copolymers (c1) and/or (c2), the powdered compositions can also contain as a cationic setting polymer copolymers (c3) that comprise, as structural units, structural units of formulas (M-11a) and (M6) as well as further structural units from the group of vinylimidazole units and further structural units from the group of acrylamide units and/or methacrylamide units.

Further particularly preferred powdered compositions are characterized in that they contain, as an additional cationic setting polymer, at least one copolymer (c3) that contains at least one structural unit in accordance with formula (M11-a) and at least one structural unit in accordance with formula (M6) and at least one structural unit in accordance with formula (M10) and at least one structural unit in accordance with formula (M12)

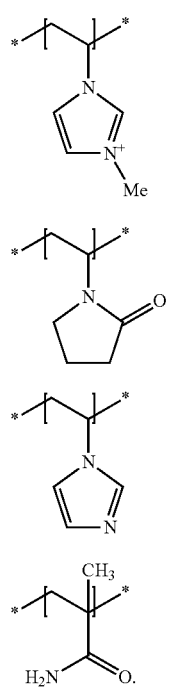

(M11-a)

(M6)

(M8)

(M12)

Here as well, it is particularly preferred if copolymers (c3) contain, besides polymer units that result from incorporation of the aforesaid structural units in accordance with formulas (M11-a), (M6), (M8), and (M12) into the copolymer, a maximum of about 5 wt %, preferably a maximum of about 1 wt % polymer units that are based on the incorporation of other monomers. Copolymers (c3) are preferably constructed exclusively from structural units of formulas (M11-a), (M6), (M8), and (M12).

All possible physiologically acceptable anions, for example chloride, bromide, hydrogen sulfate, methyl sulfate, ethyl sulfate, tetrafluoroborate, phosphate, hydrogen phosphate, dihydrogen phosphate, or p-toluenesulfonate, triflate, serve to compensate for the positive polymer charge of component (c3).

If a methosulfate is used to compensate for the positive charge of the polymer of formula (Poly3), these N-methylvinylimidazole/vinylpyrrolidone/vinylimidazole/methacrylamide copolymers are referred to according to INCI nomenclature as Polyquaternium-68 and are obtainable e.g. from BASF under the commercial name Luviquat® Supreme.

Very particularly preferred copolymers (c3) contain about 1 to about 12 mol %, preferably about 3 to about 9 mol %, and in particular about 6 mol % structural units in accordance with formula (M11-a) and about 45 to about 65 mol %, preferably about 50 to about 60 mol %, and in particular about 55 mol % structural units in accordance with formula (M6) and about 1 to about 20 mol %, preferably about 5 to about 15 mol %, and in particular about 10 mol % structural units in accordance with formula (M8) and about 20 to about 40 mol %, preferably about 25 to about 35 mol %, and in particular about 29 mol % structural units in accordance with formula (M12).

Among the additional setting polymers selected from the cationic polymers having at least one structural element of the above formula (M11-a), those considered preferred are:

vinylpyrrolidone/1-vinyl-3-methyl-1H-imidazolium chloride copolymers (for example the one having the INCI name Polyquaternium-16, under the commercial designations Luviquat® Style, Luviquat® FC 370, Luviquat® FC 550, Luviquat® FC 905, and Luviquat® HM 552 (BASF SE)), vinylpyrrolidone/1-vinyl-3-methyl-1H-imidazolium methyl sulfate copolymers (for example the one having the INCI name Polyquaternium-44, under the commercial designations Luviquat® Care (BASF SE)), vinylpyrrolidone/vinylcaprolactam/1-vinyl-3-methyl-1H-imidazolium terpolymers (for example the one having the INCI name Polyquaternium-46, under the commercial designations Luviquat® Care or Luviquat® Hold (BASF SE)), vinylpyrrolidone/methacrylamide/vinylimidazole/1-vinyl-3-methyl-1H-imidazolium methyl sulfate copolymers (for example the one having the INCI name Polyquaternium-68, under the commercial designation Luviquat® Supreme (BASF SE)), as well as mixtures of said polymers.

Further cationic polymers preferably usable in the powdered compositions contemplated herein are so-called "temporarily cationic" polymers. These polymers usually contain an amino group that, at specific pH values, is present as a quaternary ammonium group and thus cationically.

Also considered preferably suitable as temporarily cationic polymers for purposes herein are those which comprise at least one structural unit of formulas (M1-1) to (M1-8)

(M1-1)

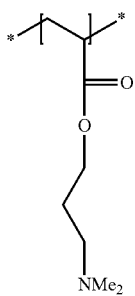 (M1-2)

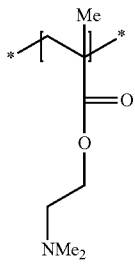 (M1-3)

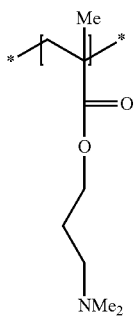 (M1-4)

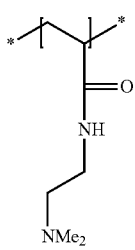 (M1-5)

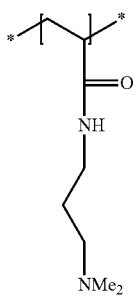 (M1-6)

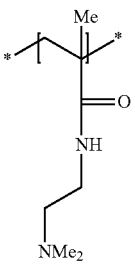 (M1-7)

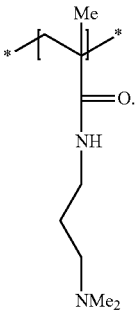 (M1-8)

Those copolymers which contain at least one structural unit of formulas (M1-1) to (M1-8) and additionally at least one structural unit of formula (M10)

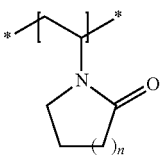 (M10)

where n signifies 1 or 3,
are in turn preferred in this context.

The group of the polymers
vinylcaprolactam/vinylpyrrolidone/dimethylaminoethyl methacrylate copolymer (for example, INCI name: Vinyl Caprolactam/PVP/Dimethylaminoethyl Methacrylate Copolymer, under the trade name Gaffix® VC 713 (ISP)),
vinylpyrrolidone/vinylcaprolactam/dimethylaminopropyl methacrylamide copolymer (e.g. INCI name: VP/Vinyl Caprolactam/DMAPA Acrylates Copolymer, under the trade name Aquaflex® SF 40 (ISP)),
vinylcaprolactam/vinylpyrrolidone/dimethylaminoethyl methacrylate copolymer (for example, as 35 to 39% solids in ethanol in the form of the commercial product Advantage LC E having the INCI name: Vinyl Caprolactam/VP/Dimethylaminoethyl Methacrylate Copolymer, Alcohol, Lauryl Pyrrolidone (ISP)),
vinylpyrrolidone/dimethylaminopropylmethacrylamide copolymer (for example, INCI name: VP/DMAPA Acrylates Copolymer, under the trade name Styleze CC-10 (ISP)),
is in turn considered a preferred list for selection therefrom of at least one or more polymers.

The powdered compositions contemplated herein can also contain at least one amphoteric setting polymer as a setting polymer. The term "amphoteric polymers" encompasses both those polymers which contain in the molecule both free amino groups and free —COOH or —SO₃H groups and are capable of forming internal salts, and zwitterionic polymers, which contain quaternary ammonium groups and —COO⁻ or —SO₃⁻ groups in the molecule, and those polymers which contain —COOH or —SO₃H groups and quaternary ammonium groups.

An example of an amphopolymer usable herein is the acrylic resin obtainable under the name Amphomer®, which represents a copolymer of tert-butylaminoethyl methacrylate, N-(1,1,3,3-tetramethylbutyl)acrylamide, and two or more monomers from the group of acrylic acid, methacrylic acid, and simple alkyl esters thereof The amphoteric setting polymers are contained in the powdered compositions preferably in quantities from about 0.01 to about 20 wt %, particularly preferably from about 0.05 to about 10 wt %, based on the total agent. Quantities from about 0.1 to about 5 wt % are very particularly preferred.

At least one anionic setting polymer can furthermore preferably be employed as setting polymers. Anionic polymers are anionic polymers that comprise carboxylate groups and/or sulfonate groups. Examples of anionic monomers of which such polymers can be made are acrylic acid, methacrylic acid, crotonic acid, maleic acid anhydride, and 2-acrylamido-2-methylpropanesulfonic acid. The acid groups can be present in this context entirely or partially as a sodium, potassium, ammonium, mono- or triethanolammonium salt.

Within this embodiment it can be preferred to use copolymers of at least one anionic monomer and at least one nonionogenic monomer. Reference is made to the substances listed above regarding the anionic monomers. Preferred nonionogenic monomers are acrylamide, methacrylamide, acrylic acid esters, methacrylic acid esters, vinylpyrrolidone, vinyl ethers, and vinyl esters.

Preferred anionic polymers are acrylic acid/acrylamide copolymers and in particular polyacrylamide copolymers with sulfonic acid group-containing monomers. A particularly preferred anionic copolymer is made up of about 70 to about 55 mol % acrylamide and about 30 to about 45 mol % 2-acrylamido-2-methylpropanesulfonic acid, the sulfonic acid group being present entirely or in part as a sodium, potassium, ammonium, mono-, or triethanolammonium salt. Further preferably usable anionic polymers are selected from at least one polymer of the group that is constituted from copolymers of vinyl acetate and crotonic acid (such as those marketed, for example, as a commercial product Aristoflex® A 60, having the INCI name VA/Crotonates Copolymer, by the CIBA company in a 60-wt % dispersion in isopropanol/water), copolymers of ethyl acrylate and methacrylic acid (such as those marketed, for example, under the trade name Luviflex® Soft with an acid number from 84 to 105, under the INCI name Acrylates Copolymer in an approx. 20- to 30-wt % dispersion in water, by the BASF SE company), polyurethanes having at least one carboxyl group (for example a copolymer of isophthalic acid, adipic acid, 1,6-hexanediol, neopentyl glycol, and isophorone diisocyanate, such as the one marketed under the trade name Luviset PUR, having the INCI name Polyurethane-1, by the BASF SE company).

The powdered compositions contemplated herein can be packaged in almost any containers. All that is necessary is to ensure that the mechanical load on the powder upon removal of the composition is not so high that the powder is already converted into liquid form upon removal of the powder. Jars, bottles, or also Tetra Paks are suitable, for example; the container can be configured, for example, with a pouring and metering apparatus.

All powdered compositions contemplated herein can be made available at least by way of the following preferred manufacturing method, which is a second exemplary embodiment:

A second embodiment is the use of a powdered composition of the first embodiment for the temporary deformation of keratin-containing fibers, in particular human hair.

A third exemplary embodiment is a method for the temporary deformation of keratin-containing fibers, in particular human hair, in which method a powdered composition in accordance with the first exemplary embodiment is exposed, during or after application onto the keratin-containing fibers, to a mechanical load, whereby the powdered composition converts into a liquid, the keratin-containing fibers are shaped before, after, or during application of the powdered composition, and/or before, after, or during the mechanical load on the powdered composition, the shape of the keratin-containing fibers is temporarily retained by means of the powdered composition converted into said liquid.

When the powdered composition is used for temporary deformation of keratinic fibers, firstly preferably the desired quantity of powdered composition is removed from the container. The composition can be placed directly onto the keratinic fibers to be treated or, for example, onto the hand. In the first case the applied powder can be exposed, directly on the keratinic fibers, to a mechanical load, for example by means of the hands, with the result that the liquid aqueous phase is released directly on the fibers and the effect of the film-forming and/or setting polymer, present in the form of particles, is produced. If the powdered composition is firstly placed onto the hand, it can then firstly be carefully distributed in the hair and in turn only then more strongly mechanically loaded, for example by deliberately massaging the powder into the hair. The result is that the liquid aqueous phase becomes released directly on the fibers, and the effect of the film-forming and/or setting polymer, present in the form of particles, is produced. An outstanding styling effect can thereby be achieved in very controlled fashion. It is of course also possible to rub the powdered composition already on the hand, and only then to apply the resulting liquid or pasty agent onto the keratinic fibers. This procedure is not preferred, however, since an essential advantage of the powdered consistency of the styling agent, namely good distribution capability, is thereby sacrificed. The powdered composition can of course also be applied using an aid, for example a paintbrush, a sponge, a cloth, a brush, or a comb.

The Examples that follow are intended to explain the subject matter herein without, however, limiting it in any way.

EXAMPLES

Unless otherwise noted, the quantity indications indicated below are to be understood as percentages by weight.

1. Production of Powdered Styling Agents

Powdered styling agents V1, E1 to E6 were produced as described below; they had the following compositions:

| Raw materials | V1 | E1 | E2 | E3 | E4 | E5 | E6 |
|---|---|---|---|---|---|---|---|
| Aerosil® R 812 S | 17.00 | 14.00 | 15.00 | 15.00 | 14.00 | 15.00 | 15.00 |
| Sodium benzoate | 0.20 | — | 0.40 | — | — | — | — |
| Citric acid monohydrate | 0.02 | — | 0.02 | — | — | — | — |
| Amphomer® | 0.05 | — | 0.05 | — | — | — | — |
| Water, demineralized | 82.73 | 8.75 | 0.10 | 0.13 | 0.40 | 0.43 | 25.50 |
| Glycerol | — | 69.65 | 19.90 | 64.87 | 80.00 | 84.57 | — |
| Sorbitol | — | — | — | — | — | — | 59.50 |
| Calcium chloride•6 H$_2$O | — | 5.00 | 15.00 | 19.40 | 5.00 | — | — |
| Sea salt, spray-dried | — | 2.00 | — | — | — | — | — |
| 2-Phenoxyethanol | — | 0.60 | — | 0.60 | 0.60 | — | — |

Composition V1 is not in accordance with the powdered compositions contemplated herein. Compositions E1 to E6 are in accordance with the powdered compositions contemplated herein.

All the constituents except for Aerosil® R 812 S and (if present) Amphomer® were mixed in a vessel. To this liquid (core) was added the hydrophobized silicon dioxide powder Aerosil® R 812 S (INCI name: Silica Silylate). After a stirring time of 30 to 45 seconds in each case, a stable powder had respectively formed. The Amphomer (if contained) was added as a solid to the stable powder, and blended in while stirring. The finished styling powder thus obtained was decanted into polyethylene bottles.

2. Utilization

In the context of a half-side test on a test subject, hair styling was performed using the aforementioned styling agents V1 and E2. The head hair was subdivided, on a half-side basis, into a right and a left half. The left half was styled using the comparison styling powder, the right half with a styling powder as contemplated herein. For this purpose, identical quantities of the respective powder were distributed into the hair. The composition was then liquefied by massaging and kneading, and the hair was brought into the desired shape using the hands.

For the composition E2 as contemplated herein, as compared with composition V1 hair having a natural shine and a full, natural feel was obtained. Retention of the hairstyle was comparable in both cases. The hair treated with V1 seemed duller and less lively, and was slightly sticky.

3. List of Raw Materials Used

The raw materials employed in the context of the Examples are defined as follows:

Aerosil® R 812 S INCI name: Silica Silylate (Evonik Degussa)

Amphomer® Amphoteric polymer having the INCI name Octylacrylamide/Acrylates/Butylaminoethyl Methacrylate Copolymer, white powder (National Starch).

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

The invention claimed is:

1. A powdered composition comprising core-shell particles whose shell contains particles of at least one hydrophobized metal oxide powder, and whose liquid core contains, based on the weight of the core, about 20.0 wt % to 100.0 wt % of at least one polyol of formula (I)

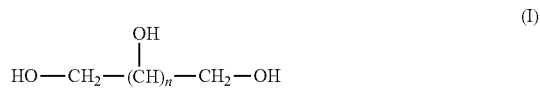

in which n denotes an integer from 1 to 4.

2. The powdered composition according to claim 1, characterized in that the hydrophobized metal oxide of the hydrophobized metal oxide powder is chosen from hydrophobized silicates, hydrophobized aluminum silicates, hydrophobized titanium dioxide, and hydrophobized silicon dioxide.

3. The powdered composition according to claim 1, characterized in that hydrophobized metal oxide powder is present in a quantity of from about 0.5 wt % to about 30 wt %, based on the weight of the total powdered composition.

4. The powdered composition according to claim 1, characterized in that the hydrophobized metal oxide powder is chosen from hydrophobized silicates, hydrophobized aluminum silicates, hydrophobized titanium dioxide, and hydrophobized silicon dioxide.

5. The powdered composition according to claim 4, characterized in that the hydrophobized metal oxide powder is silica silylate.

6. The powdered composition according to claim 1, characterized in that the polyol of formula (I) is chosen from glycerol, threitol, erythritol, sorbitol, arabitol, altritol, ribitol, xylitol, galactitol, mannitol, iditol.

7. The powdered composition according to claim 1, further containing a solvent.

8. The powdered composition according to claim 7, characterized in that the solvent is water.

9. The powdered composition according to claim 7, characterized in that the solvent is present in a quantity from 0 to about 40 wt %, based on the weight of the liquid core, in the powdered composition.

10. The powdered composition according to claim 9, characterized in that the solvent is present in a quantity from 0 to about 20 wt %, based on the weight of the liquid core, in the powdered composition.

11. The powdered composition according to claim 10, characterized in that the solvent is present in a quantity from 0 to about 10 wt %, based on the weight of the liquid core, in the powdered composition.

12. The powdered composition according to claim 1, further comprising a mineral salt.

13. The powdered composition according to claim 1, further comprising a setting polymer.

14. The powdered composition according to claim 1, characterized in that the liquid core contains, based on the weight of the core, about 50.0 wt % to 100.0 wt % of the polyol of formula (I)

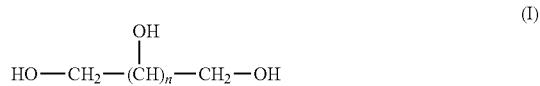

in which n denotes an integer from 1 to 4.

15. A method for the temporary deformation of keratin-containing fibers, the method comprising the steps of:

exposing a powdered composition, during or after application onto the keratin-containing fibers, to a mechanical load, whereby the powdered composition converts into a liquid, the powdered composition comprising core-shell particles whose shell contains particles of at least one hydrophobized metal oxide powder, and whose liquid core contains, based on the weight of the core, about 20.0 wt % to 100.0 wt % of at least one polyol of formula (I)

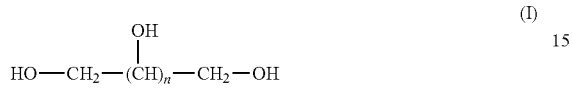

in which n denotes an integer from 1 to 4;

shaping the keratin-containing fibers
before, after, or during application of the powdered composition,
and/or
before, after, or during the mechanical load on the powdered composition,
wherein the shape of the keratin-containing fibers is temporarily retained by the powdered composition converted into said liquid.

* * * * *